US012605174B1

(12) United States Patent
Huang et al.

(10) Patent No.: US 12,605,174 B1
(45) Date of Patent: Apr. 21, 2026

(54) DISTAL THROMBECTOMY DEVICE

(71) Applicant: SUZHOU ZENITH VASCULAR SCITECH LIMITED, Jiangsu (CN)

(72) Inventors: Junchun Huang, Jiangsu (CN); Shuang Li, Jiangsu (CN); Liyou Guo, Jiangsu (CN); Jie Xia, Jiangsu (CN)

(73) Assignee: Suzhou Zenith Vascular Scitech Limited, Jiangsu (CN)

( * ) Notice: Subject to any disclaimer, the term of this patent is extended or adjusted under 35 U.S.C. 154(b) by 0 days.

(21) Appl. No.: 18/994,991

(22) PCT Filed: Jul. 31, 2024

(86) PCT No.: PCT/CN2024/108715
§ 371 (c)(1),
(2) Date: Jan. 15, 2025

(87) PCT Pub. No.: WO2025/148281
PCT Pub. Date: Jul. 17, 2025

(30) Foreign Application Priority Data

Jan. 9, 2024 (CN) .......................... 202410028529.8

(51) Int. Cl.
A61B 17/221 (2006.01)
A61B 17/00 (2006.01)
(Continued)

(52) U.S. Cl.
CPC ...... A61B 17/221 (2013.01); A61B 17/00234 (2013.01); A61B 17/3207 (2013.01);
(Continued)

(58) Field of Classification Search
CPC ........ A61B 17/221; A61B 2017/22038; A61B 17/22; A61B 2017/2212; A61B 17/22031;
(Continued)

(56) References Cited

U.S. PATENT DOCUMENTS

| 2016/0038174 A1 | 2/2016 | Bruzzi et al. |
| 2020/0029984 A1 | 1/2020 | Wang et al. |
| 2023/0063821 A1 | 3/2023 | Ganske et al. |

FOREIGN PATENT DOCUMENTS

| CN | 201079423 Y | 7/2008 |
| CN | 105662647 A | 6/2016 |

(Continued)

OTHER PUBLICATIONS

International Search Report and Written Opinion for corresponding PCT Application No. PCT/CN2024/108715, dated Nov. 7, 2024.

(Continued)

*Primary Examiner* — Katherine M Shi
(74) *Attorney, Agent, or Firm* — K&L Gates LLP

(57) ABSTRACT

A distal thrombectomy device includes a wall-contact protective umbrella and a built-in removal device. The wall-contact protective umbrella includes a pushing unit and a basket. A first end of the basket is connected to the pushing unit, and a second end of the basket is provided with an opening. The pushing unit is tubular. The wall-contact protective umbrella is configured to be located at a distal end of the aspiration catheter. The basket is provided on a side of the pushing unit away from the aspiration catheter, and the basket is configured to capture a thrombus. The built-in removal device is configured to be capable of penetrating the wall-contact protective umbrella and extending out of the opening. The built-in removal device is configured to cut and remove a thrombus to unblock the distal end of the aspiration catheter and adjacent areas of the aspiration catheter.

9 Claims, 3 Drawing Sheets

(51) Int. Cl.
    *A61B 17/3207*     (2006.01)
    *A61B 17/22*     (2006.01)

(52) U.S. Cl.
    CPC .............. *A61B 2017/00238* (2013.01); *A61B 2017/00305* (2013.01); *A61B 2017/00862* (2013.01); *A61B 2017/00867* (2013.01); *A61B 2017/22038* (2013.01); *A61B 2017/22079* (2013.01)

(58) Field of Classification Search
    CPC .. A61B 17/320783; A61B 2017/00862; A61B 2017/00867; A61B 2017/22001; A61B 2017/22034; A61B 2017/22035; A61B 2017/22065; A61B 2017/22074; A61B 2017/22079; A61B 2017/22094; A61B 2017/320741; A61F 2002/016; A61F 2230/0093; A61F 2230/008; A61F 2230/0067; A61F 2230/0006; A61F 2002/018; A61F 2/013; A61F 2/011; A61F 2/0105; A61F 2/01
    See application file for complete search history.

(56) References Cited

FOREIGN PATENT DOCUMENTS

| | | | |
|---|---|---|---|
| CN | 110575225 | A | 12/2019 |
| CN | 210185649 | U | 3/2020 |
| CN | 112494104 | A | 3/2021 |
| CN | 113907837 | A | 1/2022 |
| CN | 114886505 | A | 8/2022 |
| CN | 115024790 | A | 9/2022 |
| CN | 217886123 | U | 11/2022 |
| CN | 117731362 | A | 3/2024 |
| EP | 3539486 | A1 | 9/2019 |
| WO | 2023024257 | A1 | 3/2023 |
| WO | 2023173534 | A1 | 9/2023 |

OTHER PUBLICATIONS

First Chinese Office Action dated Jun. 21, 2024 for corresponding Chinese Application No. CN202410028529.8.

Notification to Grant Patent Right for Invention dated Jul. 17, 2024 for corresponding Chinese Application No. 202410028529.8, with English Translation.

112

12

DISTAL THROMBECTOMY DEVICE

CROSS-REFERENCES TO RELATED APPLICATIONS

This is a National Stage Application, filed under 35 U.S.C. 371, of International Patent Application No. PCT/CN2024/108715, filed on Jul. 31, 2024, which is based on and claims priority of a Chinese Patent Application filed with the China National Intellectual Property Administration on Jan. 9, 2024, with application number No. 202410028529.8, the contents of which are incorporated herein by reference in their entireties.

TECHNICAL FIELD

This application relates to the field of medical device technology, for example, to a distal thrombectomy device.

BACKGROUND

Thrombus aspiration is used in the clinical treatment of peripheral vascular embolism. After the peripheral aspiration catheter is delivered in place, the aspiration catheter will aspirate the blocking thrombus into the lumen of the aspiration catheter under the action of negative pressure and discharge it from the body to achieve thrombus removal. However, during the use of the aspiration catheter, when thrombus blockage occurs at the distal end (away from the operator's side) of the aspiration catheter or in the blood vessel in adjacent areas of the aspiration catheter, the aspiration cannot be performed, the operator is required to withdraw the aspiration catheter first, then deliver auxiliary equipment or use other methods to restore the normal aspiration operation. This process consumes a certain amount of time and energy of the operator and increases the difficulty of treatment.

SUMMARY

A distal thrombectomy device is provided according to the present application, which can clear the distal end of the aspiration catheter and its adjacent blood vessel area when the aspiration catheter is kept in a predetermined position, and can prevent the thrombus from escaping, avoid the aspiration catheter from being unable to perform aspiration, so that the operation can be carried out smoothly and the difficulty of treatment is reduced.

The present application provides a distal thrombectomy device, includes: a wall-contact protective umbrella and a built-in removal device.

The wall-contact protective umbrella includes a pushing unit and a basket. A first end of the basket is connected to the pushing unit, and a second end of the basket is provided with an opening, the pushing unit is tubular. The wall-contact protective umbrella is configured to be located at a distal end of the aspiration catheter. The basket is provided on a side of the pushing unit away from the aspiration catheter, and the basket is configured to capture a thrombus.

The built-in removal device is configured to be capable of penetrating the wall-contact protective umbrella and extending out of the opening. The built-in removal device is configured to cut and remove a thrombus to unblock the distal end of the aspiration catheter and adjacent areas of the aspiration catheter.

In some possible embodiments, the pushing unit includes a first guidewire and a catheter, the catheter is connected between the first guidewire and the basket, and an oblique cut is provided at one end of the catheter away from the basket.

In some possible embodiments, the catheter includes a first tube part and a second tube part connected to each other, the first tube part is elastic, and the second tube part is provided with the oblique cut.

In some possible embodiments, the first tube part is a coiled spring structure, and the second tube part is a polymer material structure.

In some possible embodiments, the catheter is configured as at least one of the following conditions;

an inner side of the catheter is provided with an inner membrane layer; and an outer side of the catheter is provided with an outer tube layer.

In some possible embodiments, the basket is made of memory alloy material, the basket is radially contractible and expandable, and the opening is a constricted opening.

In some possible embodiments, the built-in removal device includes a delivery guidewire assembly, a filter mesh and a distal spring connected in sequence, the distal spring is configured as an unblocking guide, and the filter mesh is configured to cut and remove a thrombus.

In some possible embodiments, the delivery guidewire assembly includes a second guidewire and a proximal spring, the proximal spring connects the second guidewire and the filter mesh, the proximal spring is supported inside the pushing unit, the proximal spring has a length greater than a length of the distal spring, and an outer diameter of the proximal spring is greater than an outer diameter of the distal spring.

In some possible embodiments, the filter mesh is made of memory alloy material. A first end of the filter mesh is fixed to the delivery guidewire assembly, and a second end of the filter mesh is slidable along a center line of the delivery guidewire assembly. The filter mesh is contractible inwardly toward the center line and expandable out away from the center line.

In some possible embodiments, an end of the distal spring away from the filter mesh is a smooth surface.

In some possible embodiments, a developing ring is provided in the filter mesh at a first end facing toward the delivery guidewire assembly, and an outer diameter of the developing ring is larger than an inner diameter of the first end of the filter mesh, so that the first end of the filter mesh is clamped between the developing ring and the delivery guidewire assembly.

In some possible embodiments, the basket is provided with at least four developing points, and a developing ring is provided between the basket and the catheter.

In some possible embodiments, the distal spring is made of a developing material.

Figure 1:
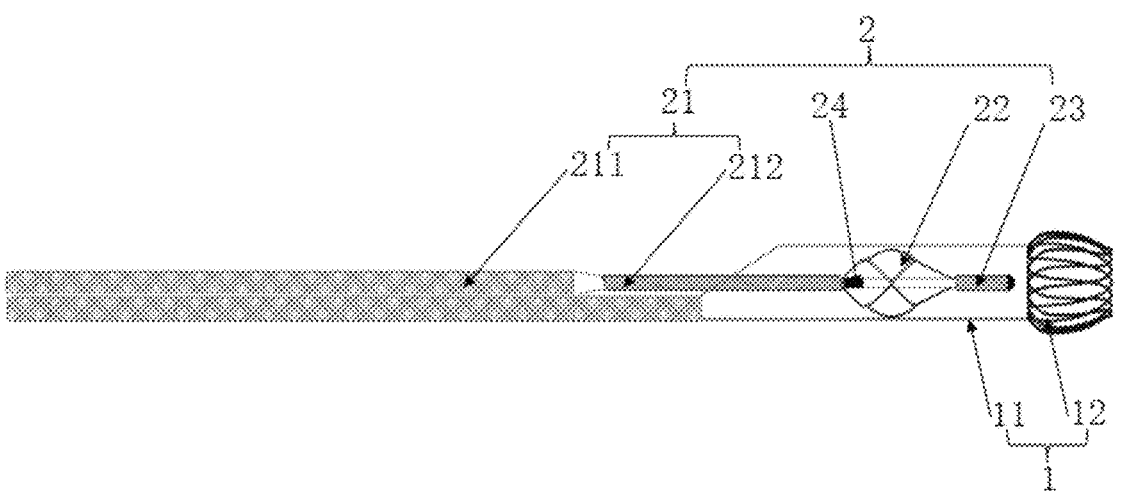
FIG. 1 is a schematic diagram of a distal thrombectomy device according to an embodiment of the present application in a use state.

REFERENCE NUMERALS LIST 1. wall-contact protective umbrella
11. pushing unit
111. first guidewire
112. catheter
1121. oblique cut
1122. first tube part
1123. second tube part
12. basket
121. opening
2. built-in removal device
21. delivery guidewire assembly
211. second guidewire
212. proximal spring
22. filter mesh
221. mesh hole
222. proximal part
223. distal part
224. Connection portion
225. inner tube
23. distal spring
24. developing ring
100. Y-shaped valve
3. aspiration catheter

DETAILED DESCRIPTION

The technical solutions of the embodiments of the present application are further described hereinafter in conjunction with the drawings. The described embodiments are only part of the embodiments of the present application rather than all of the embodiments. Based on the embodiments in the present application, all other embodiments obtained by the person skilled in the art without making creative efforts are within the scope of protection of the present application.

In the description of the present application, unless otherwise clearly specified and limited, the terms "to be connected", "connected", and "fixed" should be understood in a broad sense, for example, it can be a fixed connection, a detachable connection, or be integrally connected; it can be a mechanical connection or an electrical connection; it can be directly connected or indirectly connected through an intermediate medium, it can be the internal connection of two elements or the interaction relationship between two elements. For a person of ordinary skills in the art, the specific meanings of the above terms in the present application can be understood according to the specific circumstances.

In the present application, unless otherwise clearly specified and limited, a first feature "above" or "below" a second feature may include the first feature and the second feature being in direct contact, and it may also include the first feature and the second feature not being in direct contact but being in contact through another feature between them. Moreover, the first feature "above", "over" and "on" the second feature includes the first feature being directly above, over and on and obliquely above, over and on the second feature, or simply indicates that the first feature is higher in level than the second feature. The first feature "below", "under" and "beneath" the second feature includes the first feature being directly below, under and beneath and obliquely below, under and beneath the second feature, or simply indicates that the first feature is lower in level than the second feature.

Figure 2:
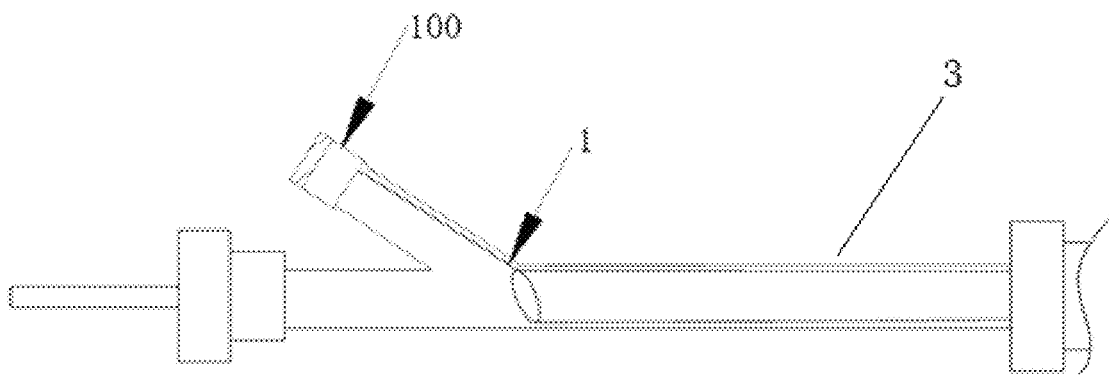
FIG. 2 is a schematic diagram of a Y-shaped valve according to an embodiment of the present application in a state of pushing a wall-contact protective umbrella.
Figure 8:
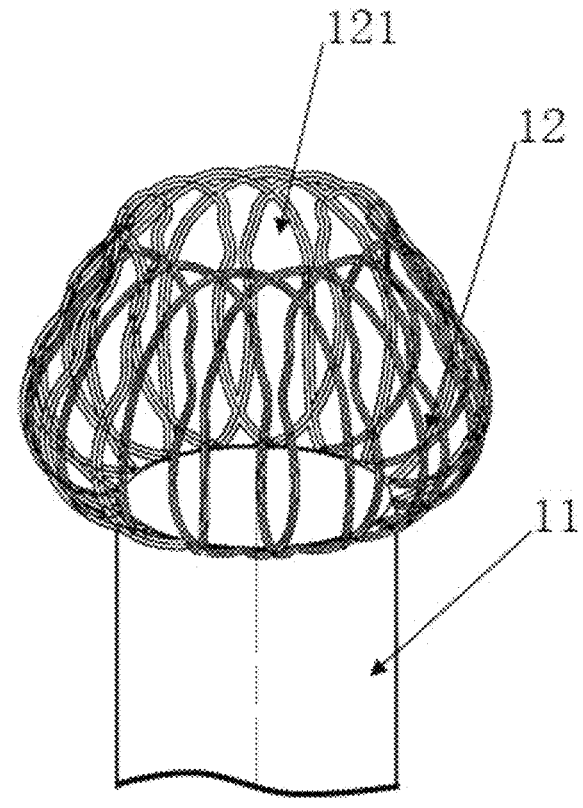
FIG. 8 is a partial schematic diagram of the wall-contact protective umbrella according to an embodiment of the present application.

As shown in FIG. 1, FIG. 2 and FIG. 8, according to embodiments of the present application, a distal thrombectomy device is provided, which is used in conjunction with an aspiration catheter 3. The distal thrombectomy device includes a wall-contact protective umbrella 1 and a built-in removal device 2. The wall-contact protective umbrella 1 includes a pushing unit 11 and a basket 12, a first end of the basket 12 is connected to the pushing unit 11, and a second end of the basket 12 is provided with an opening 121, the pushing unit 11 is tubular, the wall-contact protective umbrella 1 can be located at a distal end of the aspiration catheter 3, the basket 12 is provided on a side of the pushing unit 11 away from the aspiration catheter 3, and the basket 12 is configured to capture a thrombus. The built-in removal device 2 can penetrate the wall-contact protective umbrella 1 and can extend out of the opening 121. The built-in removal device 2 is configured to cut and remove a thrombus to unblock the distal end of the aspiration catheter 3 and its adjacent areas.

The meaning of proximal or distal is a relative position concept for the operator. The position closer to the operator is the proximal end, and the position farther from the operator is the distal end.

When in use, the wall-contact protective umbrella 1 is located at the distal end of the aspiration catheter. Due to the setting of the tubular pushing unit 11, the aspiration catheter is always kept in an unblocked state. When the aspiration catheter is working, since the basket 12 at the distal end of the wall-contact protective umbrella 1 is unfolded at the distal end, when the distal end of the aspiration catheter and its adjacent blood vessel area are blocked, the built-in removal device 2 can be pushed toward the distal end of the aspiration catheter to extend from the opening 121 of the wall-contact protective umbrella 1 to cut and remove the blocking thrombus. At this time, if the thrombus escapes, the escaped thrombus can be captured and intercepted by the basket 12, so that the distal blood vessel can be restored to be unblocked. After the operation, the operator can withdraw and remove the wall-contact protective umbrella 1 and the built-in removal device 2 together. The unblocking and thrombus interception are performed when the aspiration catheter is kept in a predetermined position without being withdrawn from the body, thereby avoiding the situation where the aspiration cannot be performed, allowing the operation to proceed smoothly and reducing the difficulty of treatment.

Figure 3:
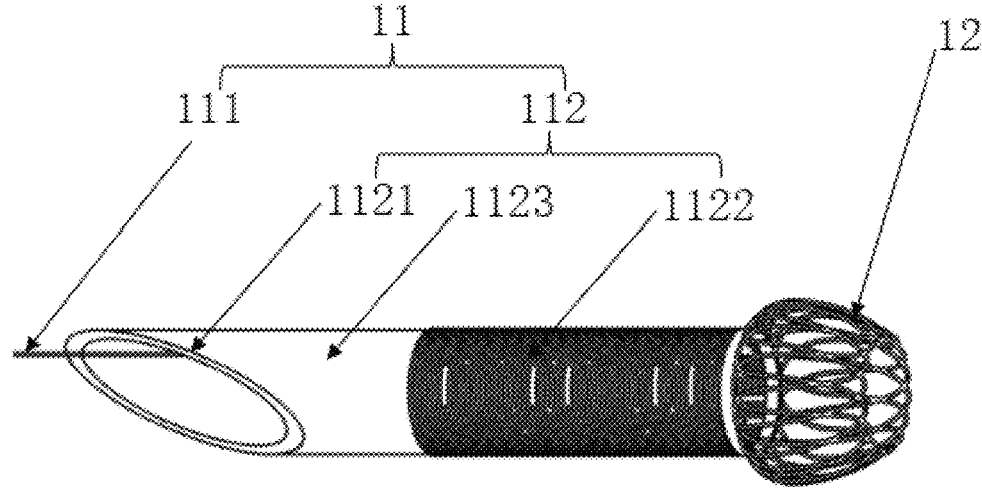
FIG. 3 is a schematic diagram of the wall-contact protective umbrella according to an embodiment of the present application.

As shown in FIG. 1 and FIG. 3, in one embodiment, the pushing unit 11 includes a first guidewire 111 and a catheter 112, both of which fit an inner wall of the blood vessel, specifically, the first guidewire 111 plays a pushing role, and the catheter 112 is connected between the first guidewire 111 and the basket 12. When used in conjunction with the aspiration catheter 3, as shown in FIG. 2, the first guidewire 111 of the wall-contact protective umbrella 1 is pushed, and the wall-contact protective umbrella 1 enters the aspiration catheter 3 from a Y-shaped valve 100. At this time, the outer side of the pushing unit 11 fit an inner wall of the aspiration catheter 3 and the pushing unit 11 can move in the aspiration catheter 3. The first guidewire 111 is continued to be pushed, the wall-contact protective umbrella 1 is pre-placed into the distal end of the aspiration catheter 3, the basket 12 is extended from the distal end of the aspiration catheter 3 and then released to expand, and the aspiration catheter 3 performs aspiration. An oblique cut 1121 is provided at one end of the catheter 112 away from the basket 12. Since the wall-contact protective umbrella 1 is provided with the oblique cut 1121, the wall-contact protective umbrella 1 will not cause blockage to the blood flow when passing through the Y-shaped valve 100, thereby reducing the surgical risk.

Figure 7:
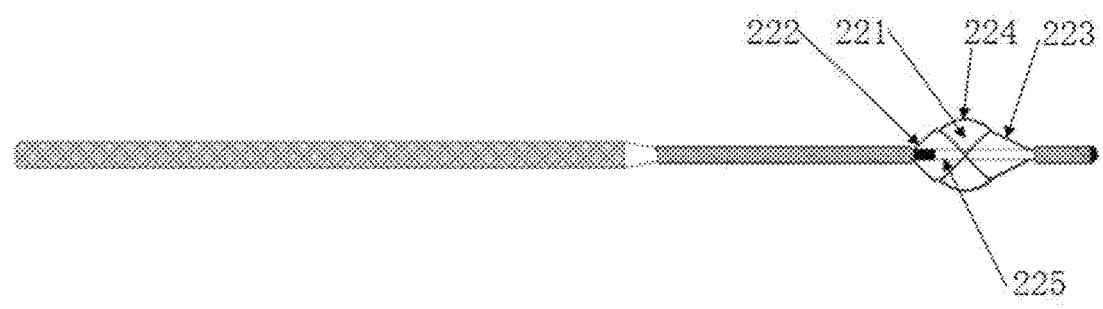
FIG. 7 is a schematic diagram of a filter mesh according to an embodiment of the present application.

As shown in FIG. 1 and FIG. 7, the built-in removal device 2 includes a delivery guidewire assembly 21, a filter mesh 22 and a distal spring 23 connected in sequence, and the distal spring 23 is configured as an unblocking guide. The distal spring 23 can pass through the thrombus and play a guiding role, which is convenient for the subsequent removal of the thrombus. The delivery guidewire assembly 21 includes a second guidewire 211 and a proximal spring 212. The proximal spring 212 connects the second guidewire 211 and the filter mesh 22. The proximal spring 212 is supported inside the pushing unit 11. The proximal spring 212 is supported inside an inner wall of the catheter 112. The proximal spring 212 plays a supporting role to ensure the stable cooperation between the built-in removal device 2 and the wall-contact protective umbrella 1.

When the distal end of the aspiration catheter 3 is blocked, the operator pushes the second guidewire 211 from the proximal end and sends the built-in removal device 2 to the distal blocked portion of the aspiration catheter 3. At this time, the distal spring 23 passes through the blockage and continues to push the built-in removal device 2 to the distal end. The filter mesh 22 reaches the blockage, and the operator pushes and pulls the second guidewire 211 to cut the blockage, negative pressure aspiration is restored or covering is performed and the thrombus is removed. In this process, thrombus escape may occur. Since the basket 12 is set at the distal end of the aspiration catheter 3, the broken thrombus will be captured by the basket 12 of the wall-contact protective umbrella 1. By withdrawing the second guidewire 211, the built-in removal device 2 covering the thrombus can be withdrawn outside the body; by withdrawing the first guidewire 111, the basket 12 closes centripetally, the captured broken thrombus are pushed to the tube end of the aspiration catheter 3 and withdrawn out of the body through negative pressure, thereby ensuring smooth aspiration during the operation without thrombus escape. After the aspiration is completed, the basket 12 is withdrawn to the proximal end of the aspiration catheter 3, and the Y-shaped valve 100 is held and withdrawn, and the wall-contact protective umbrella 1 can be withdrawn outside the body together with the aspiration catheter 3.

When performing interventional treatment for peripheral vascular embolism, the wall-contact protective umbrella 1 and the built-in removal device 2 are compressed and placed in the introduction sheath, as shown in FIG. 1: the introduction sheath is pushed to the distal position of the thrombus, the introduction sheath and the second guidewire 211 are withdrawn, and at the same time, the first guidewire 111 is kept stationary, the basket 12 of the wall-contact protective umbrella 1 is released from compression and expanded, and then the introduction sheath and the second guidewire 211 are withdrawn to the thrombus, the second guidewire 211 is kept stationary, the introduction sheath is continued to be withdrawn, and the built-in removal device 2 is released from compression to wrap the thrombus; after the interventional treatment is completed, the second guidewire 211 is withdrawn firstly to retract the built-in removal device 2 into the introduction sheath, and then the first guidewire 111 is withdrawn to retract the wall-contact protective umbrella 1 into the introduction sheath, and finally it is withdrawn from the body, thus the operation is completed. The wall-contact protective umbrella 1 and the built-in removal device 2 of the present application are assembled in the manner shown in FIG. 1, so that the built-in removal device 2 is received in the pushing unit 11 of the wall-contact protective umbrella 1. When the device is pushed to the thrombus lesion, the built-in removal device 2 and the wall-contact protective umbrella 1 can reach the thrombus at the same time, and then release by the corresponding guidewires are controlled to release the built-in removal device 2 and the wall-contact protective umbrella 1, which greatly shortens the operation time and makes the operation easier for the operator.

The first guidewire 111 and the catheter 112 are an integrated structure or separated structures. When they are separated structures, the first guidewire 111 can be plugged into the inner wall of the catheter 112. The outer diameter of the catheter 112 is slightly smaller than the inner diameter of the aspiration catheter 3, which is convenient for pushing. Specifically, the common materials of the first guidewire 111 are nickel titanium, stainless steel, platinum tungsten, platinum iridium, platinum nickel, platinum, gold, tantalum, tungsten, polyether-ether-ether-ketone (PEEK), polyamides (PA), polyethylene (PE), polytetrafluoroethylene (PTFE), etc., which can provide sufficient support, pushability, and good flexibility. The common materials of the catheter 112 can be stainless steel and nickel titanium, etc.

Figure 4:
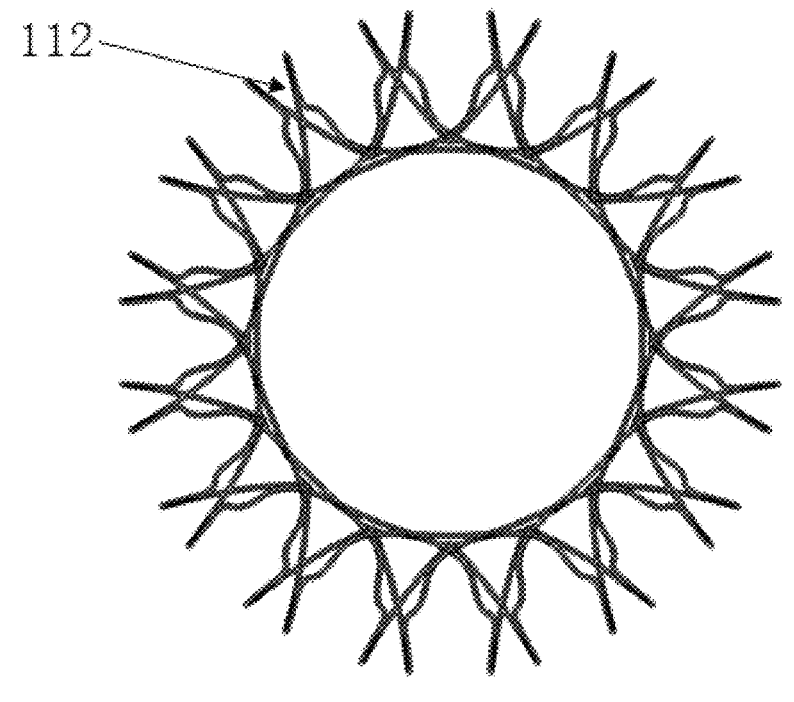
FIG. 4 is a schematic diagram of a distal end face of a catheter according to an embodiment of the present application.

As shown in FIG. 1, FIG. 3 and FIG. 4, the catheter 112 includes a first tube part 1122 and a second tube part 1123 connected to each other, the first tube part 1122 is elastic, and the second tube part 1123 is provided with the oblique cut 1121. Exemplarily, the first tube part 1122 is a coiled spring structure, formed by weaving stainless steel wire to ensure that the distal end has good flexibility. The second tube part 1123 is a polymer material structure, which can provide good support and is convenient for making the oblique cut 1121 through the polymer material during production.

The inner side of the catheter 112 is provided with an inner membrane layer (not shown in the figure) to increase the lubricity of the inner wall and passability. The inner membrane layer is a polytetrafluoroethylene (PTFE) inner membrane. The outer side of the catheter 112 is provided with an outer tube layer (not shown in the figure), and the outer tube layer is a polymer coating to increase smoothness and facilitate the pushing of the instrument.

Figure 5:
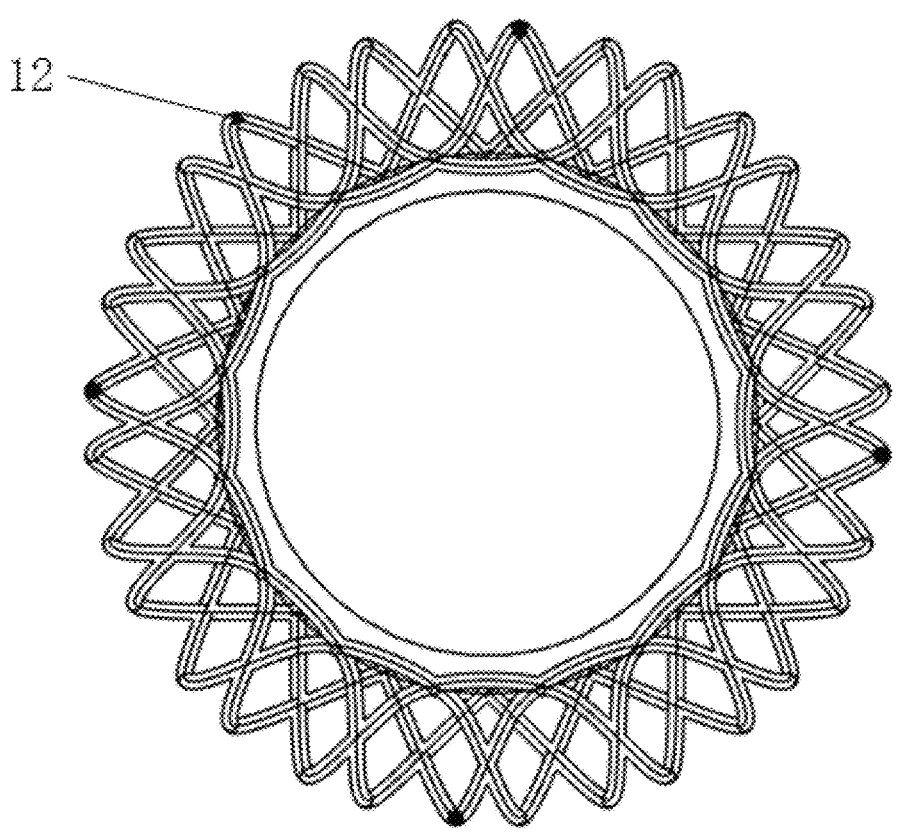
FIG. 5 is a schematic diagram of an end face of a basket according to an embodiment of the present application.

As shown in FIG. 1, FIG. 3 and FIG. 5, the basket 12 is made of memory alloy material, including but not limited to nickel-titanium alloy; the basket 12 is connected to the coiled spring structure of the catheter 112, which can be radially contract and expanded. When located in the aspiration catheter 3, the basket 12 is constrained by the aspiration catheter 3 to be in a radially contract state. When located at a distal end of the aspiration catheter 3, the basket 12 is in contact with the inner wall of the blood vessel and expanded. The opening 121 is a constricted opening, which is convenient for capturing thrombus. Optionally, the basket 12 is petal-shaped, as shown in FIG. 8, with the largest outer diameter in the middle position, and the basket 12 can be deformed according to the size of the inner wall of the blood vessel, ensuring that the outer side of the basket 12 is in contact with the inner wall of the blood vessel, further preventing the escape of thrombus. In addition, the opening 121 at the distal end of the basket 12 is a closed structure, which cooperates with the woven mesh of the basket 12, and the basket 12 can be closed as withdrawn the first guidewire 111 to push the captured thrombus to the center of the basket 12 so as to make it easier for aspiration.

The filter mesh 22 is configured to cut and remove a thrombus. The filter mesh 22 cuts the thrombus and makes it easier for aspiration. The filter mesh 22 is provided with mesh holes 221. Thrombus enter the filter mesh 22 through the mesh holes 221. The filter mesh 22 collects thrombus and removes them to the outside of the body, thereby restoring the unblocking of the blood vessel. The mesh holes 221 are quadrilateral holes.

The length of the proximal spring 212 is greater than the length of the distal spring 23. The outer diameter of the proximal spring 212 is greater than the outer diameter of the distal spring 23, so that the proximal spring 212 can provide better support to deliver the instrument into the distal passage. The distal spring 23 has better flexibility and is suitable for tortuous blood vessels, ensuring better unblocking effect. Both ends of the proximal spring 212 are fixed on the second guidewire 211. The material of the proximal spring 212 includes but is not limited to materials with good plasticity such as stainless steel, and the material of the distal spring 23 includes but is not limited to materials with developing properties such as platinum tungsten and platinum iridium, so that the whole section can be developed.

The second guidewire 211 includes but is not limited to nickel titanium, stainless steel, platinum tungsten, platinum iridium, platinum nickel, platinum, gold, tantalum, tungsten, PEEK, PA, PE, PTFE and other materials that can provide sufficient support, pushability and good flexibility, and a hydrophilic coating is present on the proximal outer surface of the second guidewire 211.

An end of the distal spring 23 away from the filter mesh 22 is a smooth surface to ensure that the distal spring 23 does not damage the blood vessel. Optionally, an end face of the distal spring 23 is a semi-sphere, or it can also be other relatively smooth shapes without edges and corners, which is not limited.

Figure 6:
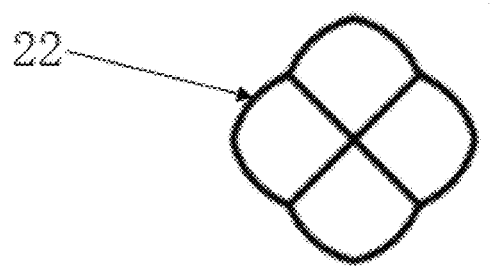
FIG. 6 is a schematic cross-sectional view of a filter mesh according to an embodiment of the present application.

As shown in FIG. 1 and FIG. 6, the filter mesh 22 is made of memory alloy material, including but not limited to nickel titanium, iron alloy and other alloy materials with shape memory properties and sufficient strength. The filter mesh 22 can be radially contract and expanded. While the built-in removal device 2 is pushed, the filter mesh 22 is in a contract state. When the built-in removal device 2 is in place, the filter mesh 22 is expanded. The built-in removal device 2 is introduced through the introduction sheath. The filter mesh 22 is in a contract state when in the introduction sheath. When the built-in removal device 2 is pushed to the wall-contact protective umbrella 1, the introduction sheath is withdrawn, and the filter mesh 22 is released from the constraint and expands. The filter mesh 22 is made by laser cutting, heat setting and surface treatment.

Optionally, a first end of the filter mesh 22 is fixed to the delivery guidewire assembly 21, and the second end can slide along the center line of the delivery guidewire assembly 21. The filter mesh 22 can be contract inwardly toward the center line and expanded out away from the center line. The filter mesh 22, the distal spring 23 and the proximal spring 212 have the same center line, the filter mesh 22 is fixed to the proximal spring 212, and the distal end of the filter mesh 22 can move along the center line, and thus the structure is more compact.

As shown in FIG. 7, in one embodiment, the filter mesh 22 includes a proximal portion 222 and a distal portion 223, the proximal portion 222 is an arc-shaped surface, the distal portion 223 is a conical surface, the proximal portion 222 and the distal portion 223 are smoothly connected, and the outer diameter of a connection portion 224 between the proximal portion 222 and the distal portion 223 is larger than the outer diameters at both ends of the filter mesh 22. The distal end of the filter mesh 22, i.e., the distal portion 223, is configured to aspirate thrombus, and has a small outer diameter and is easy to move. The middle portion, i.e., the connection portion 224, has a larger outer diameter, and is easy to collect thrombus into the proximal end, i.e., the proximal portion 222 of the filter mesh 22. In another embodiment, the filter mesh 22 is ellipsoidal in the unfolded state. By adopting the filter mesh 22 structure with small outer diameters at both ends and large outer diameter in the middle, it is easier to capture thrombus.

Optionally, an inner tube 225 is provided in the filter mesh 22, and the inner tube 225 and the filter mesh 22 have the same center line, and the inner tube 225 can be extended or shortened, and the proximal end of the inner tube 225 is fixed to the proximal end of the filter mesh 22, and the distal end of the inner tube 225 can move relative to the distal spring 23. The filter mesh 22 has cross-sectional widths of different sizes in the unfolded state, and can be adapted to wall-contact protective umbrellas 1 of different specifications.

A developing ring 24 is provided in the filter mesh 22 at a proximal end (first end) facing toward the delivery guidewire assembly 21, and the outer diameter of the developing ring 24 is larger than the inner diameter of the proximal end (first end) of the filter mesh 22, so that the first end of the filter mesh 22 is clamped between the developing ring 24 and the delivery guidewire assembly 21, which can prevent the proximal end of the filter mesh 22 from falling off and displacement, and improve the connection reliability. The developing ring 24 is sleeved and fixed to the inner tube 225.

The basket 12 is provided with at least four developing points, and a developing ring 24 is provided between the basket 12 and the catheter 112. The developing points and the developing ring 24 are positioning and developing structures to ensure that the instrument is delivered to the target point.

What is claimed is:

1. A distal thrombectomy device, comprising:

a wall-contact protective umbrella (1), comprising a pushing unit (11) and a basket (12), wherein an end of the basket (12) is connected to the pushing unit (11), and another end of the basket (12) is provided with an opening (121), the pushing unit (11) is tubular, the wall-contact protective umbrella (1) is capable of being located at a distal end of an aspiration catheter, the basket (12) is provided on a side of the pushing unit (11) away from the aspiration catheter, and the basket (12) is used to capture a thrombus; and a built-in removal device (2), capable of penetrating the wall-contact protective umbrella (1) and capable of extending out of the opening (121), wherein the built-in removal device (2) is used to cut and remove the thrombus to unblock the distal end of the aspiration catheter and adjacent areas of the distal end of the aspiration catheter;

the built-in removal device (2) comprises a delivery guidewire assembly (21), a filter mesh (22) and a distal spring (23) connected in sequence, the distal spring

(23) is used as an unblocking guide, and the filter mesh (22) is used to cut and remove the thrombus;

the delivery guidewire assembly (21) comprises a first guidewire (211) and a proximal spring (212), the proximal spring (212) connects the first guidewire (211) and the filter mesh (22), the proximal spring (212) is supported inside the pushing unit (11), the proximal spring (212) has a length greater than a length of the distal spring (23), and an outer diameter of the proximal spring (212) is greater than an outer diameter of the distal spring (23).

2. The distal thrombectomy device according to claim 1, wherein the pushing unit (11) comprises a second guidewire (111) and a catheter (112), the catheter (112) is connected between the second guidewire (111) and the basket (12), and an oblique cut (1121) is formed at one end of the catheter (112) away from the basket (12).

3. The distal thrombectomy device according to claim 2, wherein the catheter (112) comprises a first tube part (1122) and a second tube part (1123) connected to each other, the first tube part (1122) is elastic, and the second tube part (1123) is provided with the oblique cut (1121).

4. The distal thrombectomy device according to claim 3, wherein the first tube part (1122) is a coiled spring structure, and the second tube part (1123) is a polymer material structure.

5. The distal thrombectomy device according to claim 2, wherein wherein, an inner side of the catheter (112) is provided with an inner membrane layer and/or an outer side of the catheter (112) is provided with an outer tube layer.

6. The distal thrombectomy device according to claim 1, wherein the basket (12) is made of memory alloy material, the basket (12) is capable of radially contracting and expanding, and the opening (121) is a constricted opening.

7. The distal thrombectomy device according to claim 1, wherein the filter mesh (22) is made of memory alloy material, an end of the filter mesh (22) is fixed to the delivery guidewire assembly (21), another end of the filter mesh (22) is capable of sliding along a center line of the delivery guidewire assembly (21), and the filter mesh (22) is capable of contracting inward towards the center line and expanding outward away from the center line.

8. The distal thrombectomy device according to claim 1, wherein an end of the distal spring (23) away from the filter mesh (22) is a smooth surface.

9. The distal thrombectomy device according to claim 1, wherein a developing ring (24) is disposed, in the filter mesh (22), at a proximal end of the filter mesh (22) facing toward the delivery guidewire assembly (21), and an outer diameter of the developing ring (24) is larger than an inner diameter of the proximal end of the filter mesh (22), so that the filter mesh (22) is clamped between the developing ring (24) and the delivery guidewire assembly (21); and/or the basket (12) is provided with at least four developing points, and the developing ring (24) is provided between the basket (12) and a catheter (112); and/or the distal spring (23) is made of a developing material.

* * * * *